Figure 1:
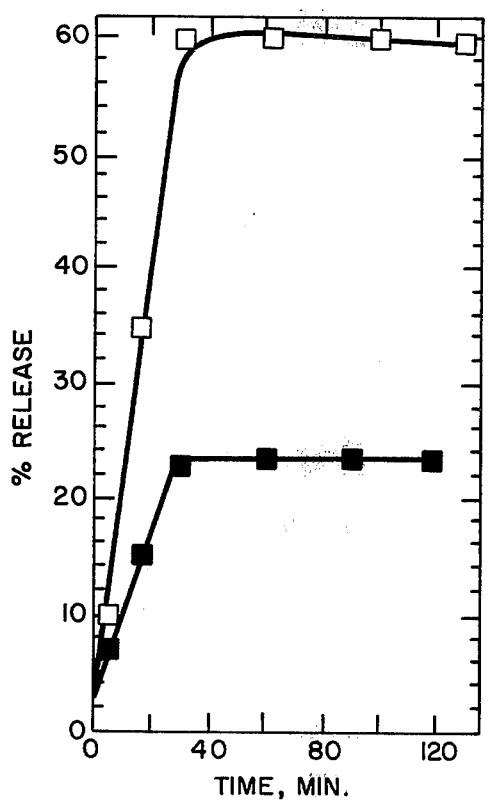

United States Patent [19]

Asher et al.

[11] 4,183,960
[45] Jan. 15, 1980

[54] DETOXIFICATION BY MEANS OF THE CONTROLLED, IN VIVO SECRETION TRIGGERED RUPTURE OF LIQUID MEMBRANE CAPSULES

[75] Inventors: William J. Asher, Fanwood; Tina C. Vogler, South Orange, both of N.J.

[73] Assignee: Exxon Research & Engineering Co., Florham Park, N.J.

[21] Appl. No.: 874,247

[22] Filed: Feb. 1, 1978

[51] Int. Cl.² .................. A61K 47/00; A61K 37/48
[52] U.S. Cl. ............................... 424/365; 424/94; 424/358
[58] Field of Search ........................... 424/365, 94

[56] References Cited

U.S. PATENT DOCUMENTS 3,932,657  1/1976  Rahman ........................... 424/365

OTHER PUBLICATIONS

Gregoriadis-FEBS Letters, vol. 36, No. 3 (Nov. 1973), pp. 292–296.

*Primary Examiner*—Sam Rosen
*Attorney, Agent, or Firm*—Joseph J. Allocca

[57] ABSTRACT

The present invention relates to liquid membrane capsules which rupture when contacted with biliary or pancreatic secretions in the intestine thereby releasing their contents in the intestine so the contents become fully available for the treatment of disease at that location in the animal or patient. Particularly, the rupturable liquid membrane capsules containing urease are used for the treatment of chronic uremia. The liquid membrane capsules comprise an internal aqueous phase which contains an oil insoluble medicinal of choice, some complexing agent, dietary supplement or enzyme particularly suited for the intended treatment. This internal aqueous and oil insoluble phase is encapsulated in a nonaqueous external phase comprising a biologically inert oil component, and a material which will complex with the biliary and/or pancreatic secretions in the intestine thereby causing the rupture of the external phase resulting in the release of the internal phase in the intestine. Thus, the internal phase is isolated during passage through the mouth, esophagus, and stomach. On the absence of this isolation the material might be an irritant or be degraded in some of these areas.

The invention is further related to a method of in vivo detoxification comprising the use of liquid membrane capsules containing detoxification materials such as medicinals and/or enzymes as an aqueous internal phase encapsulated in a continuous external phase comprising an oil which external phase further contains an additive which complexes with the biliary and/or pancreatic secretions in the intestine causing the rupture of the external phase, the detoxification process proceeding by the rupture of the external phase resulting in the release of the internal phase in the intestine. The internal phase in this case is such that it will bring about a conversion of certain toxins in the intestine to forms that can readily be trapped by conventional toxin trapping LMC as described by prior art.

12 Claims, 2 Drawing Figures

BILE, PANCREATIN CONTROLLED RELEASE

20% MONOOLEIN LMC

60% MONOOLEIN LMC

CONCENTRATIONS

| | BILE | PANCREATIN |
|---|---|---|
| □ | 10 mM | .25% |
| ■ | 4 mM | .10% |
| ○ | 0 | 0 |

DETOXIFICATION BY MEANS OF THE CONTROLLED, IN VIVO SECRETION TRIGGERED RUPTURE OF LIQUID MEMBRANE CAPSULES

The invention described herein was made in the course of or under a contract with the U.S. Department of Health, Education, and Welfare.

BRIEF DESCRIPTION OF THE INVENTION

The present invention relates to liquid membrane capsules which rupture when contacted with biliary or pancreatic secretions in the intestine thereby releasing their contents in the intestine for the treatment of disease. As an alternative, the LMC can be utilized outside the body in situations requiring the sustained release of reactants, which release is controlled by the addition of a surfactant having an HLB of 13 or greater, which surfactant complexes or solubilizes in the oil external phase thereby resulting in the rupture of that phase in the concomitant release of the aqueous internal phase. Particularly, the rupturable liquid membrane capsules are used for the treatment of chronic uremia. The liquid membrane capsules comprise an internal aqueous phase which contains an oil insoluble medicinal of choice, some complexing agent, dietary supplement or enzyme particularly suited for the intended treatment. This internal aqueous and insoluble phase is encapsulated in a nonaqueous external phase comprising a biologically inert oil component, and a material which will complex with the biliary and/or pancreatic secretion in the intestine thereby causing the rupture of the external phase resulting in the release of the internal phase in the intestine.

The invention is further related to a method of in vivo use of liquid membrane capsules containing medically active materials, i.e., medicinals and/or nontoxic toxin complexing agents and/or enzymes as an aqueous internal phase encapsulated in a continuous external phase comprising an oil which external phase further contains an additive which complexes with the biliary and/or pancreatic secretions in the intestine causing the rupture of the external phase, the beneficial process proceeding by the rupture of the external phase resulting in the release of the internal phase in the intestine.

The medically active material can operate in several ways. It can perform as a catalyst, such as an enzyme, which can convert a toxic material to nontoxic material or convert a toxic material to another material which is also toxic but can be readily trapped and removed by other ingested LMC toxin traps. In some cases of digestive diseases a catalyst is required to convert a food to a nutritionally beneficial material capable of being absorbed through the mucous of the intestine into the blood. Without the catalyst, the disease does not allow the normal digestive process to occur. In other cases of digestive disease a dietary supplement can be administered orally encapsulated in the LMC and made available in the small intestine. In the absence of encapsulation the supplement would be converted to another material in the stomach. Additionally, a drug can be administered orally, encapsulated in this LMC and delivered in the small intestine in unaltered form for adsorption and metabolism. In all of these methods the medically active material is isolated from the mouth, esophagus and stomach environments where in the absence of encapsulation the material would either cause unacceptable irritation and/or be altered to a different form with a different or no medical result.

THE INVENTION

Liquid membrane capsules containing medicinals and/or toxin traps and/or enzymes have been described in Ser. No. 775,575 filed March 8, 1977 in the names of Asher, Li and Shrier. In that application the medicinals, toxin traps and/or enzymes functioned by permeation from the aqueous internal phase through the nonaqueous external oil phase or alternatively, the toxin permeated through the external oil phase into the internal aqueous phase, therein to react with the medicinal, toxin trap or enzyme.

It has been discovered, and forms the basis of the invention that detoxification processes can be practiced in which the external oil phase of a liquid membrane capsule is ruptured due to interaction in the intestine with the biliary and/or pancreatic secretions present therein. By utilizing this bile and/or pancreatin induced rupture mechanism selective release of encapsulated medicinals and/or nontoxic toxin complexing agents and/or enzymes can be accomplished. Liquid membrane capsules are formulated which exhibit resistance to leakage in the stomach, which are mechanically strong and which exhibit negligible permeation through the external phase. These same LMC, however, are selectively ruptured in vivo by contacting with biliary and/or pancreatic secretions through the complexing of the biliary and/or pancreatic secretions with a selected component in the external phase. By use of this rupture mechanism, medicinals and/or enzymes and/or nontoxic toxin complexing agents can be utilized which ordinarily would be harmed, deactivated or otherwise altered on exposure to stomach acid or would by their very presence irritate the mouth, esophagus or stomach, since the encapsulated medicinals and/or enzymes and/or nontoxic toxin complexing agents pass relatively unaltered and uneffected through the stomach, the rupturing occurring only in the intestine. These specially formulated LMC may be used in combination with conventional LMC wherein the conventional LMC serves to adsorb to products resulting from the interaction of the components of the internal aqueous phase of the rupturable LMC with the toxins of the intestinal tract.

The LMC of the present invention are prepared by techniques known in the art. Typical preparative techniques include the addition of an aqueous solution or suspension of medicinal and/or nontoxic toxin complexing agents and/or enzyme phase to the selected oil phase under conditions of agitation resulting in the encapsulating of the aqueous phase by the oil phase resulting in the formation of an emulsion.

The oil phase typically comprises a biologically harmless oil such as mineral, paraffin, refined vegetable, refined animal oil to which may be added, if desired, a surfactant and/or strengthening agent. These surfactants and/or strengthening agents are characterized however, as being nontoxic and as not interfering with the reaction being practiced. They also must be nonreactive with the component of the external phase.

The oil external phase also contains a component which complexes with the biliary and/or pancreatic secretions resulting in the "triggered" rupture of the LMC. This component must also be nontoxic and nonreactive with the components of the internal phase.

This emulsion is in turn suspended in an aqueous suspension phase resulting in the formation of the LMC.

In general, the aqueous internal phase may contain any water soluble or water suspendable medicinal and/or non-toxic toxin complexing agents and/or enzyme, for which release in the intestine where biliary and pancreatic secretions are present is desired. Reasons why such release might be desired and materials which might be released are: sustained release over a period of time is desirable: KCL (treatment of potassium depletion in hypertension), anti-histamines such as chlorpheniramine mateate, anorexiants such as diethylpropon hydrochloride and amphetamines, aminophylline (treatment of bronchitis), trimethadione, metronidiazole, penicillin O, protection of drug from acid pH of stomach: penicillin G, amylase (enzyme for hydrolysis of starches), lepase (enzyme for the hydrolysis of triglycerides), lactase, urease; avoidance of gastric irritation: aspirin, methenamine madelate (treatment of urinary tract infection), ammonium chloride (treatment of indigestion). Many of the materials are soluble in the aqueous internal phase to from 0.0001 wt. % to about 10 wt. % at 37° C. Alternatively from 0.0001 wt. % to about 10 wt. % may be suspended in the internal aqueous phase if the materials to be used are not water soluble.

This aqueous phase is in turn suspended in a nonaqueous hydrocarbon external phase. This hydrocarbon external phase (oil phase) is designed to be immiscible with the fluids normally present in the lumen of the GI tract and to be nontoxic in the GI tract. Further, this oil phase may contain an oil soluble surfactant and/or strengthening agent so as to insure its relatively unchanged passage through the stomach to the intestines.

Returning to the oil component of the oil phase, since it is known that certain oils are toxic, they are, obviously, excluded from consideration for use. Polynuclear aromatic oils fall into this category. Further, the components of the oil external phase must also be inert with respect to the materials solubilized or suspended in the aqueous internal phase.

In selecting the oil component, it is also essential that the practitioner select one which is not digested or altered in the stomach environment. Some examples of oils which can be utilized in the LMC used in the process of the instant invention include hydrocarbon oils that are refined to remove toxic ingredients, and comprise molecular weights up to 1000, e.g. paraffins, isoparaffins, naphthenes and nonpolynuclear aromatics. Particularly desirable are the mineral oils which have been highly refined for use in human ingestion. Additionally, oils or treated oils from animal or vegetable sources may be used if they can pass unconverted through the stomach. For example, vegetable oils and animal fats that are heavily hydrogenated to contain at least 10 wt. % more hydrogen than at normal saturation may be used. Further, silicone fluids containing the repeat unit

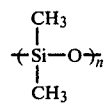

can be used. Any of these oils should have a viscosity of about 1 to about 1000 centistokes at normal body temperature. The preferable range is about 1-150 centistokes.

This oil external phase may also contain a surfactant. This component must also be nontoxic to the body, and resistant to attack in the stomach thereby preventing adverse effects in the stomach.

The oil-soluble surfactant component may be present in the exterior phase from about 0.01 wt. % up to the solubility of said surfactant in said exterior phase but not more than about 50 wt. % of said exterior phase, preferably, from about 0.5 wt. % to about 5 wt. %. A wide variety of surfactants can be used in the instant invention. These surfactants are described in "Surface Active Agents and Detergents" by Schwartz, Perry and Bush, Interscience Publishers, Inc., New York, New York, "Surface Chemistry" by Osepow, Reinhold Publishing Company, New York, New York, 1962, Chapter 8. In addition, there may be present in the oil external phase a strengthening agent (the same material which functions as the surfactant may also function as the strengthening agent).

Nonlimiting examples of strengthening agents include polyisobutylene, especially the lower molecular weight material, e.g. a molecular weight of about 900, polyisobutylene succinic anhydride-pentaaerythritol derivatives, ethylene-vinyl acetate copolymers, sulfonated butyl rubber and decylmethacrylate-vinyl pyridine copolymers.

A particularly preferred strengthening agent comprises a polyamine derivative having the general formula:

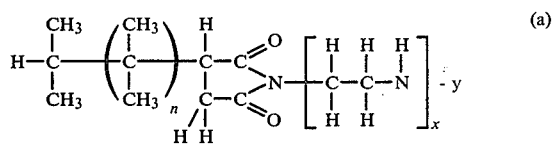

where n varies from 10 to 60, x varies 3 to 10 and y is selected from the group consisting of hydrogen and oxygen containing hydrocarbon radicals having up to 10 carbons.

These above recited compounds are useful in surfactants and are preferred surfactants for the instant invention. When embodiments of the instant invention utilize these polyamine derivatives in the dual capacity of a surfactant and strengthening agent, the overall amount of the polyamine used is adjusted accordingly. Specifically, the upper wt. % limit for the polyamine derivatives used in the dual capacity is the combined upper weight percentage limits of a surfactant and a strengthening agent when two separate components are used. The amount of strengthening agent utilized ranges from about 1 wt. % to about 40 wt. % of said exterior phase, preferably from about 1 wt. % to about 10 wt. %, most preferably from about 1 wt. % to about 5 wt. % of the exterior phase.

An essential component of the oil external phase comprises materials capable of solubilization or interaction with the bile salts and/or pancreatic secretions on the intestinal tract. These components are classified as a Class I (triglycerides, diglycerides, long chain fatty acids, medicinal ($C_6$–$C_{14}$) chain alcohols) or Class II (phospholipids, monoglycerides, "acid soaps", alphahydroxy fatty acids) polar lipids as defined by M. C. Carey and D. M. Small in "Micelle Formation by Bile Salts" in Arch. Intern. Med., Vol. 130, Oct. 1972. This component may be present in the range of from about 10–95 wt. %, the balance being oil, surfactant and/or strengthening agent. This essential component may be selected from the group consisting of, by way of non-limiting example, monoolein, vegetable oils (containing 30–80% oleic acid).

The bile solubilizer can also be present in the oil phase as an additive not responsible for the integrity of the membrane. These components should be present in the 0.1–20% composition range of the oil phase. Examples of such materials are lecithin, medium chain alcohols (i.e., n-decanol,) and oleate or monooleate containing materials. It must be noted that some of the above recited compounds may also function as surfactants in which case they should be independently present at from 0.1–20 wt. % over and above the amount required when functioning as a surfactant. Very good results are obtained when the oil phase comprises monoolein 20–80%; sorbitan monooleate 0.5–2% and the polyamine derivative (a) 2–10%.

EXAMPLES

Figure 2:
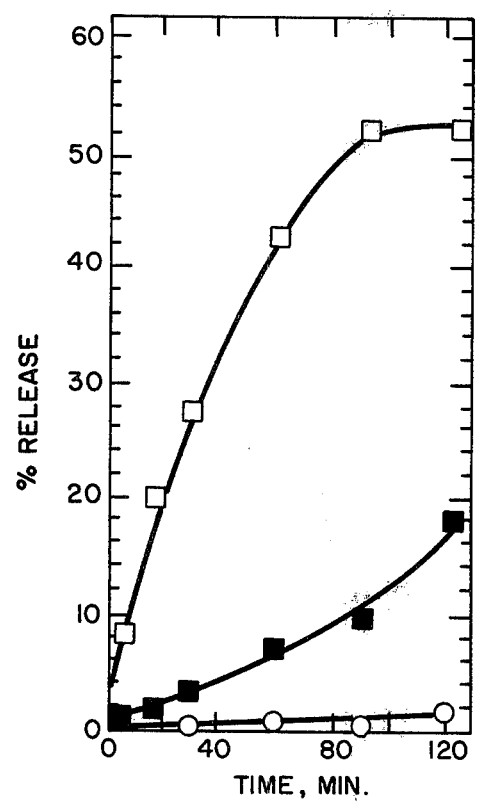

The composition of the oil phase will determine the nature of the release and the biliary and pancreatic secretion concentration the extent of the release. FIGS. 1 and 2 indicate the percent of the oil insoluble tartaric acid released from LMC with time. Note that there is very little transfer of acid in the absence of bile and pancreatin indicating that an encapsulated material would be protected from the acid in the stomach.

TABLE I

| Composition of LMC Emulsions For: | |
|---|---|
| Fig. 1: | |
| Oils: | 75% Mineral oil 87, 20% monoolein, 4% surfactant/strengthening agent (a), 1% Sorbitan monooleate |
| Internal: | 59.2% tartaric acid |
| Fig. 2: | |
| Oils: | 35% Mineral oil 87, 60% monoolein, 4% surfactant/strengthening agent (a); 1% Sorbitan monooleate |
| Internal: | 59.2% tartaric acid |
| Table II: | |
| Oils: | 35% Mineral oil 87, 60% monoolein, 4% surfactant/strengthening agent (a), 1% Sorbitan monooleate |
| Internal: | .6g urease/100 ml water |
| Table III: | |
| Oils: | 35% Mineral oil 87, 60% monoolein, 4% surfactant/strengthening agent (a), 1% sorbitan monooleate |
| Internal: | 10% urease (in buffer) |
| External Solution: | 8 g albumin<br>4 g NaHCO₃ per liter water<br>5 g NaCl<br>+ bile and pancreatin as indicated in the figures and tables. |
| Buffer Solution: | 6 g methyl cellulose, 5 g NaCl, 4 g NaHCO₃ per liter water |

The rate of release is a function of the highly correlated biliary and pancreatic secretion rates. The biliary and pancreatic secretion rates are simulated in in vivo tests using different concentrations of bile and pancreatin. The increasing rate of release with increasing secretion rates is illustrated in FIGS. 1 and 2. Some materials are either damaged or removed from the lumen of the gastrointestinal tract by these secretions. As examples, lipids are transported out of the lumen, across the mucosa after being associated with bile, and proteins are converted by the proteolytic enzymes in the pancreatic secretion. It may be desirable to maintain a concentration of a material such as an enzyme, which is, of course, a protein, in the lumen of the gastrointestinal tract. Using the system of this invention, the secretion rates which are causing the conversions deactivating the enzyme are also causing more of the encapsulated enzyme to be released. In effect, an in vivo control loop is established using the secretion rates as the moderator or controller.

As a specific example, intestinal urease is required for removal of $NH_3$ by LMC in the treatment of chronic uremia. Several of the pancreatic enzymes are proteolytic and can potentially deactivate urease in the intestine. If the urease is introduced into the intestine in liquid membranes, of controlled rupturability the deactivation of urease could be matched by release of urease from the LMC, resulting in an in vivo control loop.

Listed in Table II are activities (in terms of the rate at which $NH_3$ is produced from urea) of the external solution after contacting with LMC containing urease. (The activity does not necessarily indicate the % of urease released.)

TABLE II

| Urease Activity, mg $NH_3$ 100 ml/min | External Solution |
|---|---|
| 3.2 | .9% saline |
| 10.7 | 10mM bile, .25% pancreatin in .9% saline |

Two dogs of equal weight with Thomas cannulae in the jejunum ("proximal cannula", at entrance to small intestine, one foot downstream from the biliary and pancreatic duct) and in the ileum ("distal cannula", seven-eights distance along intestine) were administered (1) 120 ml of a buffer solution to the stomach (via stomach tube) which was later collected from the proximal cannula; (2) 120 ml of a buffer solution and 10 ml of LMC urease to the stomach (via stomach tube) which were later collected from the proximal cannula; (3) 120 ml of a buffer solution and 10 ml of urease containing LMC to the proximal which were later collected at the distal cannula. At least five infusions were performed in each of the above cases. The buffer solution collected was analyzed for urea and ammonia. When urease is present in the intestine the ratio of urea to ammonia will be lower than when urease is not present since the action of the urease is to convert urea to ammonia. Results appear in Table III.

TABLE III

| Mean $\frac{\text{Urea Concentration}}{NH_3 \text{ Concentration}}$ | Case |
|---|---|
| 3.3 | 1 |
| 2.1 | 2 |
| .89 | 3 |

What is claimed is:

1. A liquid membrane capsule (LMC) composition which ruptures only in the environment of the small intestine in response to the biliary and/or pancreatic secretions present therein, which LMC composition comprises an aqueous internal phase which has dissolved or suspended therein a medicinal, a nontoxic toxin complexing agent, an enzyme or a dietary supplement; a nonaqueous nontoxic oil external phase and an aqueous suspending phase, wherein the nonaqueous oil external phase comprises a nontoxic oil component and a material capable of solubilization by or interaction with the biliary and/or pancreatic secretions in the intestinal tract, wherein said material is a Class I or Class II polar lipid selected from the group consisting of triglycerides, diglycerides, long chain fatty acids, medicinal ($C_6$–$C_{14}$) chain alcohols, monoglycerides, acid soaps and alpha-hydroxy fatty acids.

2. The LMC compositions of claim 1 wherein the Class I and Class II polar lipids are selected from the group consisting of monoolein and vegetable oils containing 30 to 80% oleic acid.

3. The LMC compositions of claim 1 wherein the material capable of solubilization or interaction with the bile and/or pancreatin of the small intestine, is present in the nonaqueous oil external phase at a concentration ranging from 10–95% of the oil external phase.

4. The LMC compositions of claim 1 wherein the aqueous internal phase has dissolved or suspended therein a medicinal, nontoxic toxin complexing agent or enzyme.

5. The LMC composition of claim 4 wherein the medicinal, nontoxic toxin complexing agent or enzyme is present in the aqueous internal phase at a concentration of from 0.0001 wt. % to about 10 wt. %.

6. A method of in-vivo detoxification consisting of the oral ingestion of a liquid membrane capsule (LMC) composition which ruptures only in the environment of the small intestine in response to the biliary and/or pancreatic secretions present therein, which LMC composition comprises an aqueous internal phase, which aqueous internal phase has dissolved or suspended therein a medicinal, a nontoxic toxin complexing agent, an enzyme or a dietary supplement; a nonaqueous nontoxic oil external phase and an aqueous suspending phase, wherein the nonaqueous oil external phase comprises a nontoxic oil component and a material capable of solubilization by or interaction with the biliary and-/or pancreatic secretions in the tract 1 wherein said material is a Class I or Class II polar lipid selected from the group consisting of triglycerides, diglycerides, long chain fatty acids, medicinal ($C_6$–$C_{14}$) chain alcohols, monoglycerides, acid soaps and alpha-hydroxy fatty acids, resulting in the rupture of the LMC and the release thereby of the contents of the internal aqueous phase in the small intestine.

7. The method of claim 6 wherein the Class I and Class II polar lipids are selected from the group consisting of monoolein and vegetable oils containing 30 to 80% oleic acid.

8. The method of claim 6 wherein the material capable of solubilization or interaction with the bile and/or pancreatin of the small intestine is present in the nonaqueous oil external phase at a concentration ranging from 10–95% of the oil external phase.

9. The method of claim 6 wherein the medicinal, nontoxic toxin complexing agent, enzyme or dietary supplement is present in the aqueous internal phase at a concentration of from 0.0001 wt. % to about 10 wt. %.

10. The method of claim 6, 7, 8 or 9 wherein the oil component of the nonaqueous oil external phase has a viscosity between about 1 and 1000 centistokes at normal body temperature and is selected from the group consisting of vegetable oils and animal fats that are heavily hydrogenated to contain at least 10% more hydrogen than normal saturation, silicone fluids containing the repeat unit:

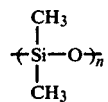

and hydrocarbon oils that are refined to remove toxic ingredients and comprise molecular weights up to 1000, selected from the group consisting of paraffins, isoparaffins, naphthenes and nonpolynuclear aromatics.

11. The method of claim 10 wherein the nonaqueous oil external phase further comprises a surfactant present at from about 0.01 wt. % up to the solubiliby of said surfactant in said exterior phase but not more than about 50 wt. % of said exterior phase.

12. The method of claim 10 or 11 wherein the nonaqueous oil external phase further comprises a strengthening agent present at from 1 wt. % to about 40 wt. % wherein said strengthening agent comprises a polyamine derivative having the general formula:

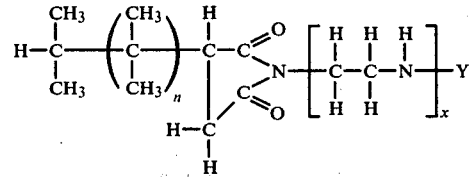

where n varies from 10 to 60, x varies from 3 to 10 and y is selected from the group consisting of hydrogen and oxygen containing hydrocarbon radicals having up to 10 carbons.

* * * * *